US008512633B2

(12) United States Patent
Cregger et al.

(10) Patent No.: US 8,512,633 B2
(45) Date of Patent: Aug. 20, 2013

(54) INDICATOR FOR MONITORING A STERILIZATION PROCESS

(75) Inventors: Tricia A. Cregger, Fairlawn, OH (US); Phillip P. Franciskovich, Concord, OH (US); Antoinette Bower, Mentor, OH (US); Randal W. Eveland, Concord, OH (US); Michael A. Centanni, Parma, OH (US)

(73) Assignee: American Sterilizer Company, Mentor, OH (US)

( * ) Notice: Subject to any disclaimer, the term of this patent is extended or adjusted under 35 U.S.C. 154(b) by 1046 days.

(21) Appl. No.: 11/839,553

(22) Filed: Aug. 16, 2007

(65) Prior Publication Data
US 2009/0047176 A1 Feb. 19, 2009

(51) Int. Cl.
*A61L 9/00* (2006.01)
(52) U.S. Cl.
USPC .................. 422/28; 422/22; 422/56; 206/439
(58) Field of Classification Search
None
See application file for complete search history.

(56) References Cited

U.S. PATENT DOCUMENTS

| | | | | |
|---|---|---|---|---|
| 3,814,668 A | | 6/1974 | Blake et al. ................. 195/103.5 |
| 4,142,899 A | * | 3/1979 | Sato et al. ...................... 430/213 |
| 4,168,779 A | * | 9/1979 | Yokokoji et al. ............... 206/439 |
| 4,181,500 A | | 1/1980 | Cowsar et al. .................. 23/230 |
| 4,303,753 A | | 12/1981 | Lam ............................... 435/14 |
| 4,621,049 A | | 11/1986 | Wang ............................. 435/14 |
| 4,990,284 A | * | 2/1991 | Lauterbach et al. ........ 252/408.1 |
| 4,992,296 A | | 2/1991 | Gibson ............................. 427/2 |
| 5,217,691 A | | 6/1993 | Greene et al. .................... 422/56 |
| 5,906,916 A | | 5/1999 | Wu .................................... 435/4 |
| 5,990,199 A | * | 11/1999 | Bealing et al. ................ 523/161 |
| 6,087,089 A | | 7/2000 | Wu |
| 6,329,207 B1 | | 12/2001 | Fricker et al. ................. 436/129 |
| 7,186,373 B2 | | 3/2007 | Centanni .......................... 422/3 |
| 7,280,441 B2 | * | 10/2007 | MacDonald et al. .......... 368/327 |
| 7,326,383 B2 | * | 2/2008 | Gunter et al. ................. 422/420 |
| 2003/0118478 A1 | | 6/2003 | Hehenberger .................. 422/56 |
| 2003/0194346 A1 | | 10/2003 | Read ............................... 422/28 |
| 2005/0019206 A1 | | 1/2005 | Centanni |
| 2006/0275170 A1 | * | 12/2006 | Ameri et al. .................... 422/22 |
| 2008/0274161 A1 | * | 11/2008 | Muratoglu et al. ........... 424/425 |

FOREIGN PATENT DOCUMENTS

| | | |
|---|---|---|
| WO | 9222806 | 12/1992 |
| WO | 9633242 | 10/1996 |
| WO | 0061200 | 10/2000 |

OTHER PUBLICATIONS

International Search Report and Written Opinion, Application No. PCT/US2008/072415, mailed Nov. 14, 2008.

* cited by examiner

*Primary Examiner* — Sally Merkling
(74) *Attorney, Agent, or Firm* — Renner, Otto, Boisselle & Sklar, LLP

(57) ABSTRACT

The disclosed invention relates to an indicator composition comprising at least one iodide salt, at least one binder, at least one carbonate salt and/or at least one sulfate salt, and at least one antioxidant. The indicator composition may contain at least one dye, complexing agent, inhibitor, and/or solvent. A sterilization indicator comprising the foregoing indicator composition is disclosed. The sterilization indicator may be used for monitoring sterilization processes involving oxidative chemistries.

35 Claims, 3 Drawing Sheets

_US 8,512,633 B2_

INDICATOR FOR MONITORING A STERILIZATION PROCESS

TECHNICAL FIELD

This invention relates to an indicator for monitoring a sterilization process. More particularly, this invention relates to indicator compositions, sterilization indicators employing the indicator compositions, and processes for using the indicators and for monitoring oxidative sterilization processes. These indicator compositions may be referred to as chemical indicators.

BACKGROUND

Chemical indicators are typically capable of detecting quantifiable amounts of active ingredients in a sterilization medium. These indicators may be placed with a load being processed. The chemical indicator may be monitored or observed after processing to ensure that the processed load has been effectively exposed to the active ingredient. The chemical indicator may include a dye that reacts with the active ingredient in the sterilization medium such as by oxidative bleaching of the dye. Upon oxidation the dye may change color or exhibit a change in color intensity based on the concentration of the active ingredient. A visible or observable change in color or color intensity may indicate that an effective sterilization has occurred. The chemical indicator may rely on an indirect mechanism to effect color change. With indirect indicators, the active ingredient may react with a first compound, which then reacts with an indicator dye to induce a color change.

SUMMARY

There are problems with the prior art chemical indicators for monitoring sterilization processes using oxidative chemistries (e.g., peracids, peroxides) due to the fact that the color change is often difficult to perceive or the end point is often difficult to determine. In addition, the transition for the color change of many prior art chemical indicators for the oxidative chemistries often occurs over both an extended time period and an extended concentration range. The present invention provides a solution to these problems. With the present invention an indicator is provided for sterilization processes employing the oxidative chemistries. This indicator provides the advantage of a more distinct color change with a shortened transition period. This provides for facilitated use and a more accurate interpretation of results.

The present invention relates to an indicator composition comprising: (a) at least one iodide salt, (b) at least one binder, (c) at least one carbonate salt, at least one sulfate salt, or a mixture thereof, and (d) at least one antioxidant. The indicator composition may further comprise (e) at least one dye, (f) at least one complexing agent, (g) at least one solvent, and/or (h) at least one inhibitor.

The invention further relates to a sterilization indicator, comprising: a support and the foregoing indicator composition supported by the support.

The invention further relates to a sterilization indicator, comprising: a support, and plurality of indicator panels supported by the support, each indicator panel comprising the foregoing indicator composition, with the proviso that the indicator composition on each panel varies sufficiently to provide for each panel to change color in response to a different sterilant exposure time.

The invention further relates to a sterilization process, comprising: exposing at least one article to be sterilized and the foregoing sterilization indicator to an oxidative sterilization medium.

The invention further relates to a process for monitoring an oxidative sterilization process, comprising exposing at least one article to be sterilized and the foregoing sterilization indicator to an oxidative sterilization medium, the indicator composition exhibiting a first color prior to exposure to the sterilization medium, and determining whether the indicator composition changes color from the first color to a second color during or after exposure to the sterilization medium.

BRIEF DESCRIPTION OF THE DRAWINGS

In the annexed drawings, like parts and features have like references.

DETAILED DESCRIPTION

Figure 1:
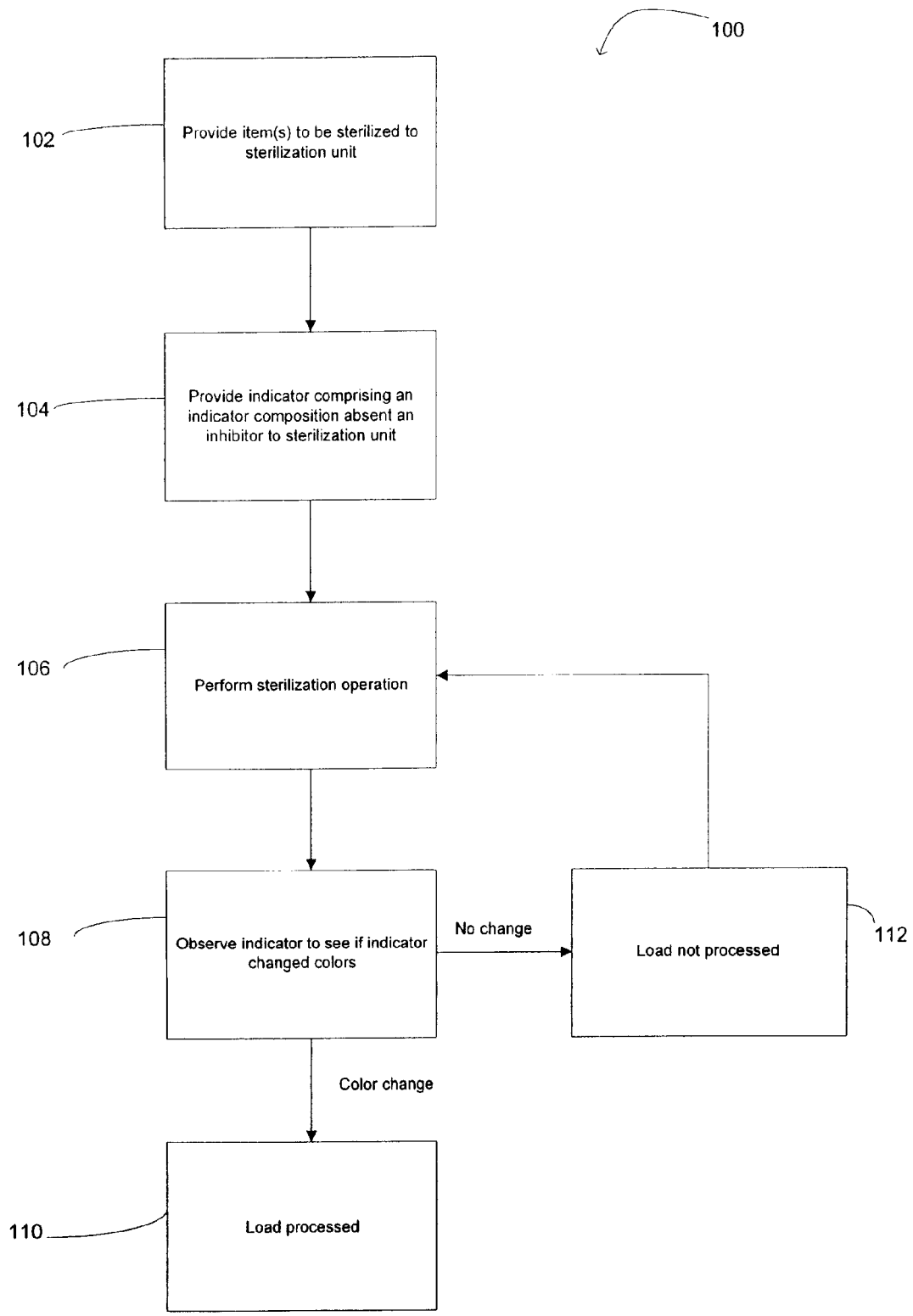
FIG. 1 is a flow chart representing an exemplary embodiment for monitoring a sterilization process in accordance with the present invention.

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

For ease of discussion, the invention is discussed herein with respect to sterilization. However, the invention may also be applicable to less rigorous processes such as disinfection, sanitization, decontamination, cleaning, and the like. The term "sterilization" may refer to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term "sterilization" may be used herein to also refer to processes less rigorous than sterilization, for example, disinfection, sanitization, decontamination, cleaning, and the like. Similarly, variations of term "sterilization," such as sterilant, sterilizing, etc., may also be used herein to refer to and encompass related variants associated with processes less rigorous than sterilization (e.g., disinfectant, disinfecting, etc.)

The inventive indicator composition and sterilization indicator described herein may be used in health care fields, scientific fields, and the like. These may be used in commercial and industrial applications where sterilization, disinfection, sanitization, decontamination, cleaning, and the like, may be desired. The commercial and industrial applications may include processes such as food processing, pasteurization, soil remediation, water remediation, and the like.

The inventive indicator composition and sterilization indicator may be used in any sterilization process in which the sterilization medium is capable of oxidizing the indicator composition to produce a color change. The sterilization process may include sterilization processes wherein the sterilization medium or sterilant may comprise one or more gaseous sterilants, one or more liquid sterilants, and the like.

Suitable gaseous sterilants may comprise peroxides including, but not limited to, gaseous hydrogen peroxide, and the like. Suitable liquid sterilants may comprise peracids including, but not limited to, peracetic acid, liquid peroxide, including, but not limited to, liquid hydrogen peroxide, and the like.

The indicator composition may be in the form of a dispersion (e.g., an emulsion) or a solution. The indicator composition may comprise an organic solvent-based or water-based composition, that is, the solvent (g) may comprise an organic liquid, water, or a mixture thereof. The term "solvent" is used herein to refer to true solvents wherein the remaining ingredients in the indicator composition may be dissolved, as well as to water-based or organic-based mediums (e.g., emulsions) wherein some or all of the ingredients may be dispersed but not necessarily dissolved. The indicator composition may be in the form of a solid wherein the solvent has been removed, for example, by evaporation. The indicator composition may be in the form of a deposit or a film layer. The deposit or film layer may be supported by a support, for example, the support used with the inventive sterilization indicator.

The indicator composition may be capable of undergoing a color change when in the presence of one or more active ingredients of a sterilization medium. The nature of the color change or the conditions under which color change occurs may be selected as desired for a particular purpose or intended use. The color change may be effected or controlled by whether the indicator composition includes a dye and/or inhibitor. For example, in one embodiment, the indicator composition may not include a dye, and the color change may result from the oxidative reaction of the iodide salt with the active ingredient. In one embodiment, the indicator composition may include at least one dye, and the color may change from a first color to a second color. In one embodiment, the indicator composition may include an inhibitor that inhibits a known or threshold concentration of active ingredient and prevents the iodide salt or iodide salt/dye combination from reacting with the active ingredient until the known or threshold active ingredient concentration has been reached.

The iodide salt (a) may comprise one or more alkali metal iodides, for example, potassium iodide, sodium iodide, lithium iodide, or a mixture of two or more thereof. In one embodiment, the iodide salt may comprise potassium iodide. The concentration of iodide salt in the indicator composition may be in the range from about 0.1 to about 10 percent by weight, and in one embodiment in the range from about 0.2 to about 5 percent by weight. The iodide salt may change color from a colorless to a colored state when in the presence of an oxidative species such as an active ingredient or sterilant (e.g., a peracid, peroxide, or the like) in the sterilization medium. For example, potassium iodide may change from a colorless state to a blue-black color upon oxidation.

The binder (b) may be used to bind the indicator composition to a support to form the sterilization indicator. The binder may comprise one or more polymeric resins. The particular resin or resins may not be limited except to the extent that the binder should not interfere with the function of the iodide salt (a). The binder (b) may comprise one or more cellulose-based polymers such as, for example, ethyl cellulose, hydroxypropylmethyl cellulose, and the like. The binder may comprise a polyamide, polypropylene, polyethylene, polystyrene, polyethylene terephthlate, or a mixture of two or more thereof, and the like. The binder may be present in the indicator composition at a concentration in the range from about 0.1 to about 40 percent by weight based on the weight of the indicator composition, and in one embodiment in the range from 1 to about 40 percent by weight, and in one embodiment in the range from about 4 to about 30 percent by weight.

The carbonate salt and/or sulfate salt (c) may comprise one or more alkali and/or alkaline earth metal salts. Examples of suitable carbonate salts may include calcium carbonate, sodium carbonate, and the like. Examples of suitable sulfate salts may include calcium sulfate, magnesium sulfate, and the like. The carbonate salt and/or sulfate salt may function as buffers to adjust the pH of the indicator composition. Changes in the salt concentration may alter the depth of the color change that occurs upon oxidation. The salts (c) may be present in the indicator composition at a concentration in the range from about 0.001 to about 10 percent by weight, and in one embodiment in the range from about 0.03 to about 4 percent by weight.

The antioxidant (d) may be used to prevent the indicator composition components from being oxidized prior to exposure to the sterilization medium. Additionally, antioxidants, such as ascorbic acid, may act as an inhibitor for the active oxidative agent. For example, an antioxidant may be desirable to prevent air oxidation of a component in the indicator composition. That is, an antioxidant may be desirable to provide a longer "shelf life" to the indicator composition. The antioxidant may comprise ascorbic acid, sodium thiosulfate, phenol acids, flavonoids, carotenes, glutathione, tocopherol, ethylenediaminetetraacetic acid (EDTA), tert-butyl hydroquinone, oxalic acid, uric acid, phytic acid, xanthones, retinol, lignan, curcumin, or a mixture of two or more thereof, and the like. The indicator composition may comprise from about 0.001 to about 25 percent by weight, and in one embodiment from about 0.1 to about 20 percent by weight, and in one embodiment from about 1 to about 15 percent by weight.

The dye (e) may be employed to provide an alternative color change to the color change obtained with an indicator composition that only uses one or more iodide salts. Any suitable dye may be used. The dye may be selected for a particular purpose or intended use to provide a desired color change in the presence of an active ingredient in the sterilization medium. The dye may comprise an oxidative dye that changes from a first color to a second color in the presence of an active ingredient in the sterilization medium. The dye may comprise indigo carmine, methyl violet, murexide, crystal violet, pararosaniline, brilliant green, cresol red, mordant blue 3, acid violet 17, alkali blue 6B, patent blue A, aniline blue, basic fuchsin, brilliant blue, brilliant cresyl blue, bromochlorophenol blue, malachite green, bromocresol green, carmine, or a mixture of two or more thereof. Indigo carmine, for example, may initially exhibit a blue color and change to brown upon exposure to an oxidative sterilant. The oxidative dye may be present in the indicator composition at a concentration in the range up to about 10 percent by weight based on weight of the indicator composition, and in one embodiment in the range from about 0.001 to about 10 percent by weight, and in one embodiment in the range from about 0.001 to about 5 percent by weight, and in one embodiment from about 0.002 to about 1 percent by weight, and in one embodiment from about 0.005 to about 0.1 percent by weight.

The dye (e) may comprise at least one non-oxidative dye. Examples of the non-oxidative dyes may include bromothymol blue, alizarin derivatives, acridine dyes, azure derivatives, bromocresol purple, resazurin, toluidine blue O, rhodamine derivatives, fluorescein derivatives, acid blue dyes, or a mixture of two or more thereof. One or more non-oxidative dyes may be used in combination with one or more oxidative dyes. The non-oxidative dye may be used to produce a selected color change in combination with one or more iodide salts and/or one or more oxidative dyes. For example, upon exposure to an oxidative sterilant, an oxidative dye or iodide salt may change color from a first color to a second color. A non-oxidative dye, however, may retain its color when exposed to an oxidative sterilant. Employing a non-oxidative dye may allow for producing a color different than that produced from the oxidative dye or iodide salt. Upon exposure to an oxidative sterilant, an oxidative dye may change from a first color to a second color, and the non-oxidative dye may mix with the second color to form a third color. Combinations of oxidative dyes and non-oxidative dyes may be selected as desired to provide a desired color change upon exposure to an oxidative sterilant. The concentration of non-oxidative dye in the indicator composition may be in the range up to about 10 percent by weight of the indicator composition, and in one embodiment in the range from about 0.001 to about 10 percent by weight, and in one embodiment in the range from about 0.001 to about 5 percent by weight, and in one embodiment from about 0.002 to about 1 percent by weight.

The complexing agent (f) may further comprise at least one complexing agent for complexing or reacting with the one or more iodide salts to enhance color upon interaction with the active ingredient in the sterilization medium or to select a color to monitor the sterilization process. For example, the color resulting from the oxidation reaction with the active ingredient may produce a color that is dependent upon the particular complex and/or product formed by the iodide salt and the complexing agent. The complexing agent may comprise one or more sugars, for example, glucose, dextrose, maltose, sucrose, lactose, xylose, fructose, starch, or a mixture of two or more thereof. The complexing agent may comprise one or more polymers, for example, one or more cellulose-based polymers and/or polyvinylpyrrolidone polymers, including one or more copolymers comprising polyvinylpyrrolidone. The complexing agent may comprise one or more cellulose substrates. Mixtures of two or more of the foregoing complexing agents may be used. The amount of complexing agent may be selected as desired to provide a complex and/or product that produces a desired color or color intensity upon exposure to the active ingredient (or desired concentration of the active ingredient) in the sterilization medium. The complexing agent may be present in the indicator composition at a concentration in the range up to about 40 percent by weight based on the weight of the indicator composition, and in one embodiment in the range from about 5 to about 40 percent by weight, and in one embodiment in the range from about 5 to about 30 percent by weight, and in one embodiment in the range from about 10 to about 25 percent by weight.

In one embodiment, the indicator composition may be characterized by the absence of the foregoing complexing agents and/or dyes.

The solvent (g) may comprise water, at least one organic solvent, or a mixture (e.g., emulsion) thereof. The organic solvent may comprise one or more alcohols, esters, ketones, or a mixture of two or more thereof, and the like. Examples of the organic solvents may include methanol, ethanol, isopropanol, acetone, methyl ethyl ketone, methoxyethanol, or a mixture of two or more thereof. The solvent may be selected based on the manufacturing application. For example, an organic solvent may be well suited for ink-based applications such as silk screening or flexographic printing. Water-based formulations may be suitable for dip strip applications. The concentration of solvent in the indicator composition may be in the range up to about 98 percent by weight, and in one embodiment in the range from about 20 to about 98 percent by weight, and in one embodiment in the range from about 50 to about 95 percent by weight.

The inhibitor (h) may be used to inhibit a predetermined amount of active ingredient in the sterilization medium. The inhibitor may be used to prevent components in the indicator composition from reacting with an active ingredient in the sterilant until a threshold level of the active ingredient is reached or unless a threshold level of active ingredient is present in the environment being tested. The inhibitor may be selected based on the active ingredient in the sterilization medium being monitored. Suitable inhibitors for peracids such as peracetic acid, may include sodium thiosulfate, heavy metal salts including ferrous salts, copper salts, cobalt salts, and the like, hydroquinone, hydroquinone derivatives, t-butyl catechol, alkanolamines such as ethanolamine, phenols, and mixtures of two or more thereof. Suitable inhibitors for peroxides, such as hydrogen peroxide, may include catalase, quinines, potassium cyanide, 2,6-di-tert-butyl-p-cresol, or a mixture of two or more thereof. In one embodiment, the inhibitor may comprise sodium thiosulfate. The inhibitor may be provided in an amount necessary to inhibit a selected suboptimal concentration of active ingredient. The concentration of inhibitor in the indicator composition may be in the range up to about 20 percent by weight based on the weight of the inhibitor composition, and in one embodiment in the range from about 0.002 to about 20 percent by weight, and in one embodiment in the range from about 0.002 to about 15 percent by weight, and in one embodiment in the range from about 0.1 to about 5 percent by weight.

In one embodiment, the indicator composition may be characterized by the absence of a thiosulfate, for example, an alkali and/or alkaline earth metal thiosulfate such as sodium thiosulfate. In one embodiment, the indicator composition may be characterized by the absence of starch. In one embodiment, the indicator composition may be characterized by the absence of thiosulfate and starch.

The inventive sterilization indicator may be prepared by applying the indicator composition to a support. The indicator composition may be in the form of a deposit or a film supported by the support. The support may not be limited in any manner except to the extent that the sterilization medium should be permitted to contact the indicator composition. The support may comprise one or more polymeric materials, paper, woven fibers, nonwoven fibers, or a combination thereof, and the like. The polymeric materials may comprise one or more polyesters, polyethylenes, polypropylenes, polystyrenes, or mixtures of two or more thereof, and the like. The support may be selected as desired for a particular purpose or intended use. For example, an indicator composition may be applied to a support suitable for use as a dip strip, in which the support would be dipped into an oxidative sterilization medium to test for the presence of any or a desired level of active ingredient. In one embodiment, the support may be provided as a strip for placement in an oxidative environment during a processing operation. Generally, the indicator composition may be applied to a support by any suitable manufacturing technique including, but not limited to, immersion, spraying, printing or coating by flexographic, gravure, screen or die processes, and the like. The support may include a first side and an opposing second side, and the indicator composition may be applied to one or both sides of the support. Depending on the nature of the support, the indicator composition may comprise a coating adhered to a surface of the support. The indicator composition may be partially or fully sorbed by the support. Upon application of the indicator composition to the support, the solvent may be partially or completely removed (e.g., by evaporation), prior to using the sterilization indicator to monitor a sterilization process. The sterilization indicator may be in the form of a test strip, label, self-contained biological indicator (SCBI), autoclave tape, or a combination thereof, and the like.

The support may be combined with one or more backing layers to provide a desired level of flexibility or rigidity to the support. The backing layers may also be made of a polymeric material, paper, woven fibers and/or non-woven fibers. The support may be attached to the backing using an adhesive or by sonic welding or heat sealing methods. The support or support/backing combination may have a label-like or tape-like construction. The support may include an adhesive applied to the surface opposite that on which the indicator composition is positioned. The adhesive may be applied to the backing layer. The adhesive may be used to attach the sterilization indicator to (1) a specific location in a process chamber or apparatus, or (2) an article to be subjected to a sterilization medium.

The sterilization indicator may further comprise a transparent vapor permeable film overlying the indicator composition. This film may be suitable for preventing water soluble components from washing out of the indicator composition. Materials suitable for use as the vapor permeable film may include, but are not limited to, polymethacrylate, polypropylene, polyethylene, polyethylene terephthalate, tyvek, mylar, and the like. The indicator composition may be in the form of a film layer, and the transparent vapor permeable film may be laminated to the indicator composition film layer.

Figure 3:
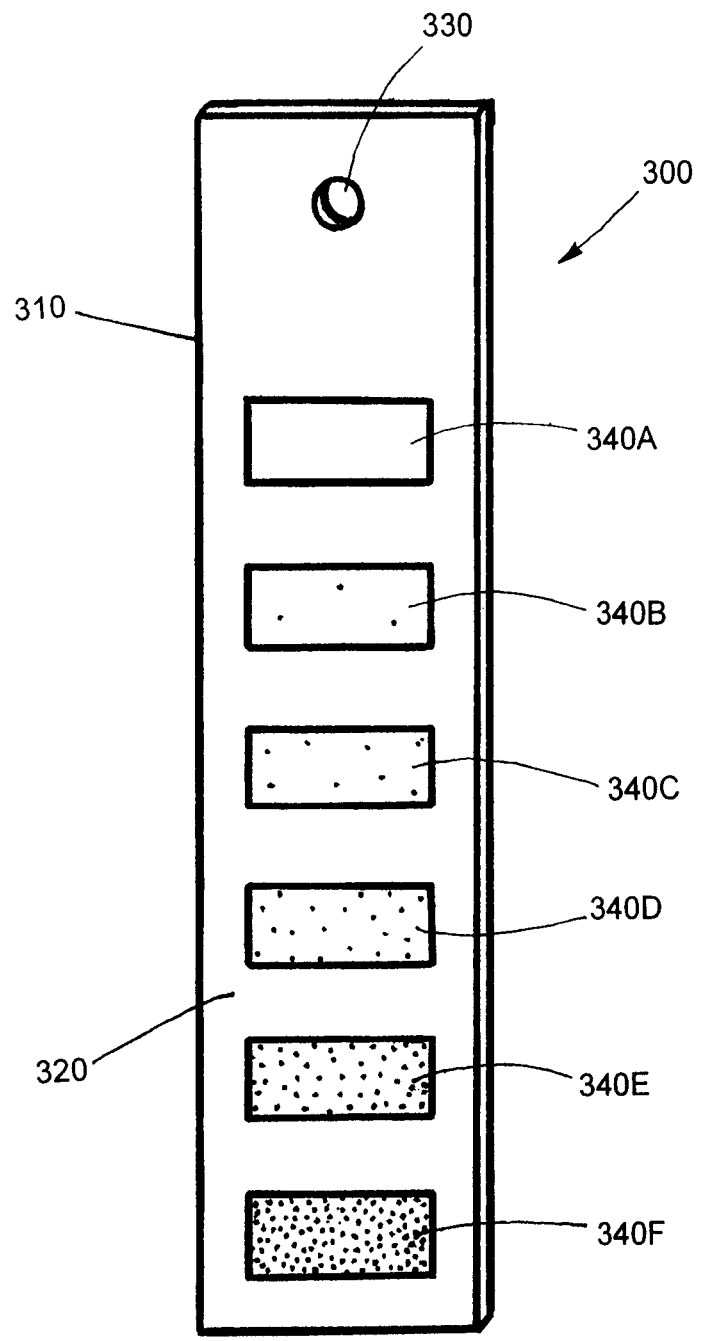
FIG. 3 is a schematic illustration of a sterilization indicator provided for in accordance with the invention.

The sterilization indicator may comprise a visual detector such as the visual detector 300 illustrated in FIG. 3. Referring to FIG. 3, the visual detector 300 includes support strip 310 which includes hole 330 to facilitate suspension of support strip. The support 310 includes indicator panels 340A, 340B, 340C, 340D, 340E and 340F. Although six indicator panels 340A-F are illustrated, it will be understood that any desired number of indicator panels 340 may be used, for example, from 1 to about 50, and in one embodiment from about 2 to about 25, and in one embodiment from about 3 to about 10 indicator panels 340. Each indicator panel 340 may comprise an indicator composition, or a substrate and an indicator composition supported by the substrate. The support strip 310 and the substrate may be made of any of the materials discussed above for making the support. The panels 340 may be used to form an incremental gradient indicator wherein each panel has a slightly different indicator composition so that each indicator panel 340 changes color after a different exposure time to the sterilant. For example, each indicator panel may comprise an indicator composition with a different concentration of inhibitor. The inhibitor in each indicator panel may be used to prevent the indicator composition from reacting with an active ingredient in the sterilant until a threshold level of the active ingredient is present in the environment being tested. Thus, an indicator panel with a relatively low concentration of inhibitor would change color relatively fast. Those with higher levels of inhibitor would change color more slowly. In the illustrated embodiment, indicator panel 340A may have a relatively low concentration of inhibitor allowing it to change color after $\Delta t$ minutes of exposure to a desired average concentration of sterilant. Likewise, indicator panels 340B, 340C, 340D, 340E, and 340F may have relatively higher concentrations of inhibitor allowing them to respectively change color after $2\Delta t$, $3\Delta t$, $4\Delta t$, $5\Delta t$, and $6\Delta t$ minutes of exposure to a desired concentration of sterilant.

The sterilization indicator may be suitable for monitoring a variety of processes involving oxidizing sterilants. This may include monitoring or evaluating a variety of active ingredients including, but not limited to, peracids and/or peroxides. The peracids may include acids having the formula $R_1CO_3H$, wherein $R_1$ is hydrogen, alkyl, cycloalkyl, phenyl, or the like. $R_1$ may contain up to about 20 carbon atoms, and in one embodiment from 1 to about 6 carbon atoms. In one embodiment, the indicator may be employed to monitor an oxidative environment or process employing peracetic acid as an active ingredient. Non-limiting examples of peroxides may include, but are not limited to, peroxides having the formula $R_2OOH$, wherein $R_2$ is hydrogen, alkyl, cycloalkyl, or the like. $R_2$ may contain from 1 to about 9 carbon atoms, and in one embodiment from 1 to about 4 carbon atoms. The peroxide may be hydrogen peroxide wherein $R_2$ is hydrogen. The sterilization indicator may be suitable for use in a variety of sterilization processes, including vaporous or liquid hydrogen peroxide sterilization processes, and liquid peracetic acid sterilization processes.

The inventive sterilization indicator may comprise an indicator composition for use with a liquid sterilization process employing peracetic acid as the active ingredient. The indicator composition may comprise at least one oxidative dye (e.g., indigo carmine, methyl violet, mureoxide, and the like), at least one iodide salt, calcium carbonate, ethyl cellulose, ascorbic acid, and at least one solvent. The solvent may be methoxyethanol. Calcium sulfate or magnesium sulfate may be substituted for the calcium carbonate. Sodium thiosulfate may be substituted for the ascorbic acid. This indicator composition may be referred to as a quantitative indicator composition.

The inventive sterilization indicator may comprise a dip strip sterilization indicator. This indicator may comprise an indicator composition comprising at least one oxidative dye (e.g., indigo carmine, methyl violet, mureoxide, and the like), at least one iodide salt, calcium carbonate, hydroxypropylmethyl cellulose (or other water soluble binder or polymer), ascorbic acid, and water.

The inventive sterilization indicator may be used with a vaporous hydrogen peroxide sterilization system. This indicator may comprise an indicator composition comprising at least one iodide salt, sodium carbonate, ethyl cellulose, ascorbic acid, and at least one organic solvent. Alternatively, the indicator composition may comprise a water-based indicator composition in which the organic solvent is replaced by water and the ethyl cellulose is replaced by a water soluble binder, such as hydroxypropylmethyl cellulose.

The sterilization indicators and indicator compositions provided for herein may be used for qualitatively and/or quantitatively monitoring oxidative sterilization processes.

The indicator composition may exhibit a color change from a first color to a second color upon exposure to an active ingredient (or optionally a threshold level of active ingredient). The first color may be any color, which may include the absence of visible color (i.e., colorless). The second color may be sufficiently different than the first color such that a color contrast from the first color to the second color may be observed. When the indicator composition has a first color that is colorless, the first color may appear as the color of the substrate (e.g., colorless, white, etc.) underlying the indicator composition. The term "color" may encompass a number of aspects of color such as hue, lightness, saturation, and the like, where one color may be different from another color if the two colors differ in at least one aspect. For example, two colors which have the same hue and saturation but have a different lightness would be considered to be different colors. Any suitable color (e.g., red, white, black, gray, yellow, purple, etc.) may be used to produce a color contrast as long as the second color can be observed. The color contrast may change (e.g., diminish). The term "color contrast" may encompass any degree of color contrast sufficient to render a color change from the first color to the second color discernable to the observer regardless of whether the color contrast changes or is constant during the visible time. The first and second colors may be selected as desired by the materials used in the indicator component such as, for example, an oxidative dye and/or a non-oxidative dye.

The indicator composition may exhibit a distinct color change within a relatively short transition period. The color change may be readily visible to the process operator. The transition period may be in the range from about 1 second to about 60 minutes, and in one embodiment from about 5 seconds to about 20 minutes, and in one embodiment from about 10 seconds to about 10 minutes, and in one embodiment from about 20 seconds to about 5 minutes, and in one embodiment from about 30 seconds to about 2 minutes. The transition period may be adjusted or controlled by varying the components in the indicator composition. For example, varying the concentration of the binder and/or the inhibitor may vary both the length of the transition period and the exposure time required for the onset of the transition to occur.

The inventive sterilization indicators may be capable of detecting semi-quantifiable to quantifiable amounts of the active ingredient in a sterilization process. The sterilization indicators may be placed within a load being processed. The sterilization indicator may be monitored or observed after processing to ensure that the processed load is effectively exposed to the active ingredient.

The inventive indicator compositions may be used to quantitatively evaluate a sterilization process to determine if a processing cycle achieved the appropriate conditions for sterilization. In particular, an active ingredient may need to be present at a particular minimum concentration to achieve sterilization. For example, a sanitizing medium employing hydrogen peroxide may require a minimum hydrogen peroxide concentration of about 500 ppm to effectively sanitize equipment. On the other hand, to sterilize medical equipment using peracetic acid, it may be necessary to employ peracetic acid at a minimum concentration of at least about 2300 ppm. The inventive indicator composition may be used to indicate that the sterilizing medium contains the appropriate concentration of active ingredient.

A sterilization indicator comprising an indicator composition may be employed qualitatively as a process indicator to monitor whether a load has been subjected to a sterilization medium. The testing may be performed on sterilization systems employing either a liquid phase sterilization medium (e.g., peracetic acid or $H_2O_2$) or a vapor phase sterilization medium (e.g., $H_2O_2$). The process is illustrated in FIG. 1. Referring to FIG. 1, a process 100 for monitoring a sterilization process using a sterilization indicator may comprise providing an item or items to be sterilized in a sterilization unit, as indicated in box 102. The sterilization indicator comprising an indicator composition is also provided to the sterilization unit, as shown in box 104. The indicator composition may comprise at least one iodide salt, at least one binder, at least one carbonate salt and/or sulfate salt, and at least one solvent. The indicator composition may be characterized by the absence of an inhibitor. The sterilization process may then be performed, as shown in box 106, utilizing a sterilization medium comprising an active ingredient (e.g., peracid or peroxide).

After the sterilization process has been completed, the sterilization indicator may be observed to see if any color change has occurred, as shown in box 108. If the sterilization indicator has changed colors, the load has been processed, as shown in box 110. That is, the indicator shows that that the load has been processed by being subjected to an oxidative environment sufficient to produce a color change in the indicator composition. This process, however, may not indicate that the appropriate conditions for sterilization have been achieved. The use of a sterilization indicator in accordance with the present invention as a process indicator may allow for distinguishing between items that have been processed and those that have not, and may be useful in conjunction with self-contained biological indicators and/or loads that are to be sterile stored.

If no color change is observed, then the load was not processed or not subjected to a sterilization medium, as shown in box 112. In such a situation, the sterilization medium may need to be replenished or changed and the load reprocessed (returning, for example, to box 106).

Figure 2:
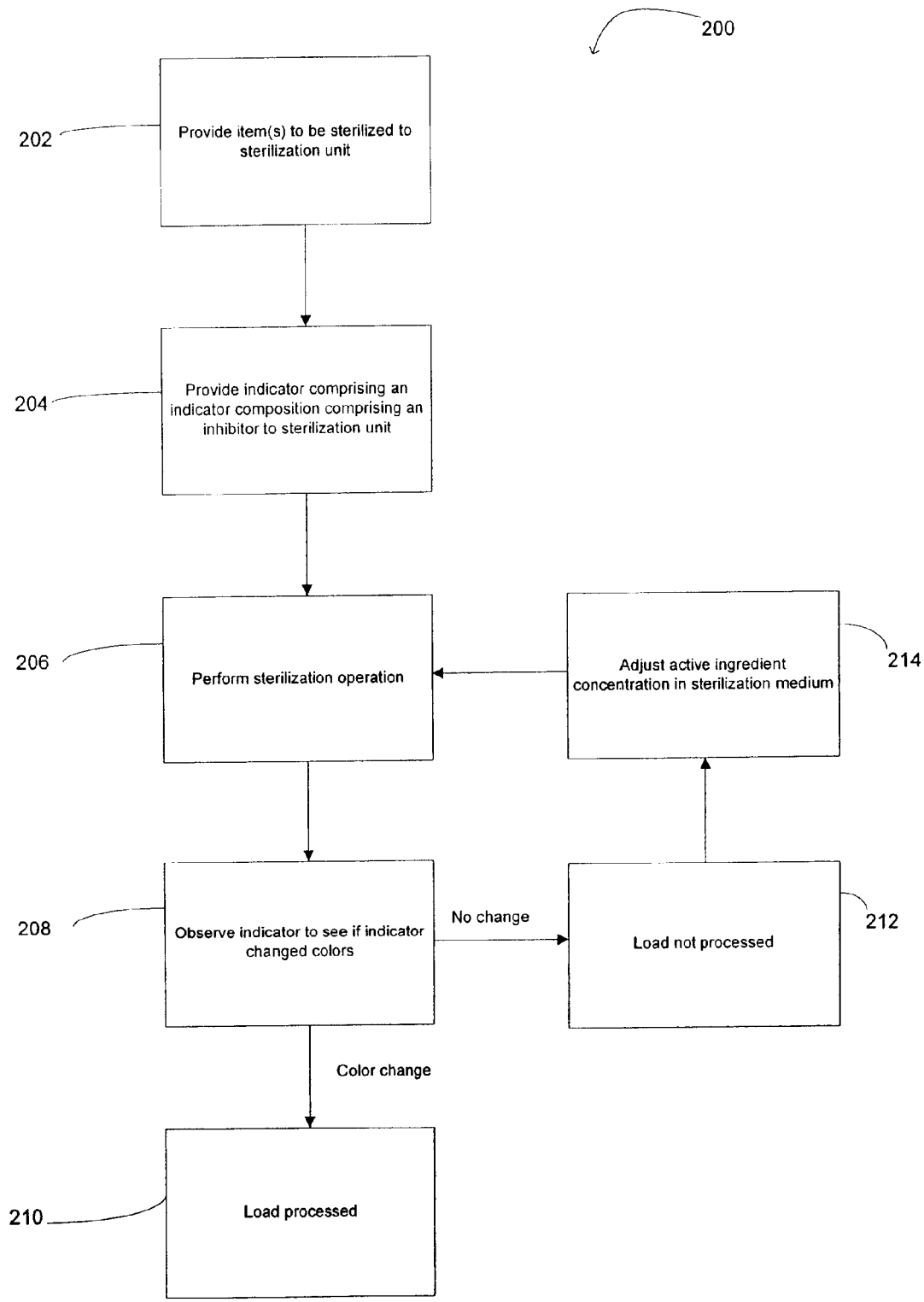
FIG. 2 is a flow chart representing an alternate embodiment for monitoring a sterilization process in accordance with the present disclosure invention.

The sterilization indicator may be employed to semi-quantitatively or quantitatively monitor a sterilization process. This may be done online (in situ) or offline. Online monitoring may be performed with liquid phase or vapor phase sterilization mediums. A sterilization process employing in situ monitoring may be conducted as illustrated in FIG. 2. Referring to FIG. 2, sterilization process 200 may be performed by providing an item or items to be sterilized (as shown in box 202) and a sterilization indicator (as shown in box 204) to a sterilization unit. The sterilization indicator, in this embodiment, comprises an inhibitor to inhibit an active ingredient in the sterilization medium. A sterilization process is performed utilizing a sterilization medium comprising an active ingredient (e.g., peracid or peroxide), as shown in box 206. After processing, the sterilization indicator is observed, as indicated in box 208, to see if the sterilization indicator has changed colors. A color change may indicate that the load was processed with a desired or threshold level of active ingredient, as indicated in box 210. If no color change is observed, then the load was not processed under the desired conditions, as indicated in box 212. Typically, the concentration of active ingredient in the sterilization medium would then be adjusted, as indicated in box 214, to provide the desired concentration of active ingredient. The load would then be subjected to another processing cycle (such as by returning to the operation in box 206) and the process may again be monitored with a new or fresh indicator to see if the desired sterilization conditions were met.

In the process illustrated in FIG. 2, the sterilization indicator may be used off-line to test the sterilization medium prior to or after performing the sterilization process.

The invention may be further understood with reference to the following examples. The examples are intended to demonstrate more specific embodiments of the invention and are not intended to be limiting in any manner.

EXAMPLES

Indicator Compositions

Example 1

An indicator composition for an ink based application is prepared using the following components:

| Component | Concentration (% by weight) |
|---|---|
| Potassium iodide | 1.7% |
| Calcium carbonate | 0.8% |

-continued

| Component | Concentration (% by weight) |
|---|---|
| Ethyl cellulose | 17% |
| Ascorbic acid | 0.3% |
| Methyoxyethanol | 80% |

Example 2

An indicator composition for an ink based application similar to that of Example 1 is prepared, but with the addition of indigo carmine in an amount of 0.02 percent by weight. The solvent concentration is adjusted to accommodate the addition of the indigo carmine.

Examples 3-8

Indicator compositions for dip strip applications are prepared as indicated below (all percentages are by weight):

| Component | Example 3 | Example 4 | Example 5 | Example 6 | Example 7 | Example 8 |
|---|---|---|---|---|---|---|
| Potassium iodide | 2% | 1% | 1% | 2% | 1% | 1% |
| Indigo carmine | 0.02% | 0.05% | 0.05% | 0.05% | 0.02% | 0.02% |
| Calcium carbonate or calcium sulfate | 0.5% $CaSO_4$ | 0.5% $CaSO_4$ | 1% $CaSO_4$ | 0.5% $CaCO_3$ | 0.5% $CaCO_3$ | 1% $CaCO_3$ |
| Hydroxypropylmethyl cellulose | 20% | 20% | 20% | 20% | 20% | 20% |
| Ascorbic acid | 2% | 2% | 3% | 3% | 3% | 3% |
| Water | Balance | Balance | Balance | Balance | Balance | Balance |

Process Monitoring
Sterilization Indicators 1-4

The ink based indicator compositions of Examples 1 and 2 may be utilized to make sterilization indicators for testing in a sterilization environment. Specifically, sterilization indicators are prepared by applying the indicator composition of Example 1 or Example 2 to a support. Each dry component in the formulation is weighed out. The solvent is then added and the dry components are stirred until fully mixed making an ink. The ink is then placed on the support by a screen printing method. The ink is dried, either by heating or by exposure to ambient air, to remove any excess solvent. A transparent vapor permeable laminate film is adhered across the printed ink with an inert silicon-based adhesive. Sterilization indicators 1 and 3 comprise the indicator composition of Example 1, and sterilization indicators 2 and 4 comprise the indicator compositions of Example 2.

Sterilization indicators 1 and 2 are subjected to a sterilization process under the following conditions. Sterilization indicators 1 and 2 are placed into a liquid peracetic acid based sterile processing system, such as a STERIS SYSTEM 1, and held by a transfer clip. The chemistry is added to the system and the cycle is initiated. During the cycle, peracetic acid contacts the printed ink indicator. The peracetic acid oxidizes the colorless iodide ion into a colored iodine complex. For sterilization indicator 1, the indicator is initially colorless but upon exposure to a sufficient concentration of the sterilizing agent changes to a yellow-brown color. Sterilization indicator 2 is initially a blue color that turns brown upon exposure to the sterilizing agent.

Sterilization indicators 3 and 4 are subjected to a sterilization process utilizing STERIS's Reliance EPS processor. Sterilization indicators 3 and 4 are placed into a liquid peracetic acid based endoscope reprocessing system, and held by a transfer clip. The chemistry cup is added to the system and the cycle is initiated. During the cycle, peracetic acid is generated to sufficient levels for high level disinfection to occur. The generated peracetic acid, with a concentration 1800 ppm peracetic acid, contacts the printed ink indicator. The peracetic acid oxidizes the colorless iodide ion into a colored iodine complex. Sterilization indicator 3 is initially colorless but upon exposure to a sufficient concentration of the sterilizing agent changes from colorless to yellow-brown. Sterilization indicator 4 is initially a blue color that turns brown upon exposure to the sterilizing agent.

Sterilization Indicators 5-10

Sterilization indicators 5-10 are prepared by placing indicator compositions 3-8, respectively, on a support. Each dry component in the formulation is weighed out. The water (solvent) is then added and the dry components are stirred until fully mixed making an ink. The ink is applied to a support by submersion in a dip tank, by spraying onto the substrate, or by printing methods. The support is rapidly dried using heat. The sterilization indicators are then subjected to a sterilization environment using vaporized hydrogen peroxide at a concentration from less than 1 mg/l to 6-10 mg/l hydrogen peroxide. Sterilization indicators 5-10 are initially a blue color. Upon exposure to sterilization conditions, the indicators change to various shades of brown depending upon the indicator composition that is used. Higher concentrations of indigo carmine result in a deeper blue color that requires a higher concentration of hydrogen peroxide to fully change color from blue to brown. Higher concentrations of the potassium iodide result in a deeper brown endpoint color.

While the invention has been explained with reference to various embodiments, it is to be understood that various modifications thereof may become apparent to those skilled in the art upon reading the specification. Therefore, it is to be understood that the invention that is covered includes such modifications as may fall within the scope of the appended claims.

The invention claimed is:
1. An indicator composition, comprising:
 (a) at least one iodide salt,
 (b) at lease one binder,
 (c) at least one carbonate salt, at least one sulfate salt, or a mixture thereof, and
 (d) at least one antioxidant, comprising ascorbic acid, phenol acid, flavonoid, carotene, glutathione, tocopherol, ethylenediaminetetraacetic acid, tert-butyl hydroquinone, oxalic acid, uric acid, phytic acid, xanthone, retinol, lignan, curcumin, or a mixture of two or more thereof,
 wherein the indicator composition further comprises
 (h) at least one inhibitor present, the indicator composition provided on each of a plurality of panels on a support, wherein each panel contains a different amount of the at least one inhibitor, and the amount of the at least one inhibitor present on each panel is sufficient to prevent the iodide salt from reacting with an active ingredient in a sterilization medium until a selected threshold concentration of the active ingredient is reached or unless a selected threshold concentration of the active ingredient is present at each of the plurality of panels, a change in color of the indicator composition from a first color to a second color indicating that the active ingredient is present at a concentration in excess of the selected threshold concentration and wherein the at least one inhibitor comprises a ferrous salt, a copper salt, a cobalt salt, hydroquinone, a hydroquinone derivative, t-butyl catechol, an alkanolamine, catalase, quinine, potassium cyanide, 2,6-di-tert-butyl-p-cresol, or a mixture of two or more thereof.

2. The indicator composition according to claim 1, wherein the indicator composition further comprises (e) at least one dye.

3. The indicator composition according to claim 1, wherein the indicator composition further comprises (f) at least one complexing agent.

4. The indicator composition according to claim 1, wherein the indicator composition further comprises (g) at least one solvent.

5. The indicator composition according to claim 1 wherein the iodide salt comprises one or more alkali metal salts.

6. The indicator composition according to claim 1 wherein the iodide salt comprises sodium iodide, potassium iodide, lithium iodide, or a mixture of two or more thereof.

7. The indicator composition according to claim 1, wherein the binder comprises one or more cellulose-based polymers.

8. The indicator composition of claim 1, wherein the binder comprises polyamide, polypropylene, polyethylene, polystyrene, polyethylene terephthalate, or a mixture of two or more thereof.

9. The indicator composition according to claim 1, wherein the carbonate salt comprises an alkali and/or alkaline earth metal salt.

10. The indicator composition according to claim 1, wherein the sulfate salt comprises an alkali and/or alkaline earth metal salt.

11. The indicator composition according to claim 1, wherein the carbonate salt comprises calcium carbonate, sodium carbonate, or a mixture thereof.

12. The indicator composition according to claim 1, wherein the sulfate salt comprises calcium sulfate, magnesium sulfate, or a mixture thereof.

13. The indicator composition according to claim 2, wherein the dye comprises at least one oxidative dye, at least one non-oxidative dye, or a mixture thereof.

14. The indicator composition according to claim 2, wherein the dye comprises indigo carmine, methyl violet, murexide, crystal violet, pararosaniline, brilliant green, cresol red, mordant blue 3, acid violet 17, alkali blue 6B, patent blue A, aniline blue, basic fuchsin, brilliant blue, brilliant cresyl blue, bromochlorophenol blue, malachite green, bromocresol green, carmine, or a mixture of two or more thereof.

15. The indicator composition according to claim 3, wherein the complexing agent comprises at least one sugar, at least one polymer, or at least one cellulose substrate.

16. The indicator composition according to claim 3, wherein the complexing agent comprises glucose, dextrose, maltose, sucrose, lactose, xylose, fructose, starch, a cellulose-based polymer, a polyvinylpyrrolidone polymer, or a mixture of two or more thereof.

17. The indicator composition according to claim 4, wherein the solvent comprises water, at least one organic solvent, or a mixture thereof.

18. A sterilization indicator, comprising: a support, and the indicator composition of claim 1 supported by the support.

19. The sterilization indicator according to claim 18, wherein the support comprises one or more polymeric materials, paper, woven fibers, non-woven fibers, or a combination of two or more thereof.

20. The sterilization indicator according to claim 19, wherein the polymeric material comprises one or more polyesters, polyethylenes, polypropylenes, polystyrenes, or a mixture of two or more thereof.

21. The sterilization indicator according to claim 18, wherein the indicator composition is applied to the support using immersion, spraying, flexographic coating, gravure coating, screen coating, die coating, or a combination of two or more thereof.

22. The sterilization indicator according to claim 18, wherein the support comprises one or more backing layers.

23. The sterilization indicator according to claim 18, wherein the support comprises a first surface, a second surface opposite the first surface, the indicator composition being applied to the first surface, and an adhesive being applied to the second surface.

24. The sterilization indicator according to claim 18, wherein a transparent vapor permeable film overlies the indicator composition.

25. A sterilization indicator, comprising: a support, and plurality of indicator panels supported by support, each indicator panel comprising the indicator composition of claim 1, with the proviso that the indicator composition on each panel varies sufficiently to provide for each panel to change color in response to a different sterilant exposure time.

26. A sterilization process, comprising: exposing at least one article to be sterilized and the indicator of claim 18 to an oxidative sterilization medium.

27. The process according to claim 26, wherein the sterilization medium comprises at least one liquid sterilant.

28. The process according to claim 26, wherein the sterilization medium comprises at least one gaseous sterilant.

29. The process according to claim 26, wherein the sterilization medium comprises liquid and/or vaporous hydrogen peroxide.

30. The process according to claim 26, wherein the sterilization medium comprises peracetic acid.

31. A process for monitoring an oxidative sterilization process, comprising:
  exposing at least one article to be sterilized and the sterilization indicator of claim 18 to an oxidative sterilization medium, the indicator composition exhibiting a first color prior to exposure to the sterilization medium, and
  determining whether the indicator composition changes color from the first color to a second color during or after exposure to the sterilization medium.

32. The process according to claim 31, wherein the sterilization indicator is used as a process indicator, and a change from the first color to the second color indicates that the at least one article to be sterilized has been exposed to a sterilant.

33. The process according to claim 31, wherein the composition further comprises at least one inhibitor selected to inhibit a selected concentration of the sterilant, a change in color from the first color to the second color indicating that the sterilant is present at a concentration in excess of the selected concentration.

34. The indicator composition of claim 1 wherein the active ingredient comprises an oxidant.

35. The indicator composition of claim 1 wherein the at least one inhibitor is selected based on the active ingredient in the sterilization medium.

* * * * *